United States Patent
Rajasekharan et al.

(10) Patent No.: US 12,313,618 B2
(45) Date of Patent: May 27, 2025

(54) PREDICTIVE MODEL FOR WATER QUALITY DETERIORATION

(71) Applicant: Hach Company, Loveland, CO (US)

(72) Inventors: Vishnu Vardhanan Rajasekharan, Fort Collins, CO (US); Russell Young, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 720 days.

(21) Appl. No.: 17/174,851

(22) Filed: Feb. 12, 2021

(65) Prior Publication Data
US 2022/0260547 A1  Aug. 18, 2022

(51) Int. Cl.
| | | |
|---|---|---|
| *G01N 33/18* | (2006.01) | |
| *C02F 1/00* | (2023.01) | |
| *C02F 3/30* | (2023.01) | |
| *G06N 7/00* | (2023.01) | |

(52) U.S. Cl.
CPC ........... *G01N 33/188* (2013.01); *C02F 1/006* (2013.01); *C02F 3/303* (2013.01); *G06N 7/00* (2013.01); *C02F 2209/02* (2013.01); *C02F 2209/06* (2013.01); *C02F 2209/14* (2013.01); *C02F 2209/29* (2013.01); *C02F 2209/36* (2013.01)

(58) Field of Classification Search
CPC ....... G01N 33/188; C02F 1/006; C02F 1/008; C02F 1/76; C02F 3/303; C02F 2209/02; C02F 2209/06; C02F 2209/14; C02F 2209/29; C02F 2209/36; C02F 2209/008; C02F 2209/006; C02F 2209/001; C02F 2209/15; C02F 2307/14; C02F 9/00; C02F 2209/04; C02F 2303/04; C02F 2101/16; C02F 3/302
See application file for complete search history.

(56) References Cited

U.S. PATENT DOCUMENTS

| | | | |
|---|---|---|---|
| 9,970,903 B1 | 5/2018 | Gerardi et al. | |
| 2003/0023534 A1 | 1/2003 | Kadambe | |
| 2005/0173262 A1* | 8/2005 | Nakanishi | C02F 1/4676 205/743 |
| 2005/0192963 A1 | 9/2005 | Tschiegg et al. | |
| 2007/0138091 A1* | 6/2007 | Yamasaki | C02F 3/223 210/620 |
| 2010/0143187 A1* | 6/2010 | Reimann-Philipp | G01N 33/18 422/3 |
| 2010/0274637 A1 | 10/2010 | Li et al. | |

(Continued)

FOREIGN PATENT DOCUMENTS

WO  WO2020043872 A1  3/2020

*Primary Examiner* — Mohammad K Islam
(74) *Attorney, Agent, or Firm* — Ference & Associates LLC

(57) ABSTRACT

An embodiment provides a method of forecasting water quality deterioration in a water distribution system, including: receiving, at an electronic device, a data set comprising measured values of a plurality of components within the water distribution system; determining, based upon algorithmic analysis of the measured values, a water quality index; and providing, based on the determined water quality index, a recommendation to mitigate water quality deterioration in the water distribution system. Other aspects are described and claimed.

16 Claims, 5 Drawing Sheets

(56) References Cited

U.S. PATENT DOCUMENTS

| | | | |
|---|---|---|---|
| 2011/0015913 A1* | 1/2011 | Yamashita | C02F 3/341 |
| | | | 703/11 |
| 2013/0297529 A1* | 11/2013 | Shirazi | G06Q 40/06 |
| | | | 705/36 R |
| 2017/0061309 A1 | 3/2017 | Wasserkrug et al. | |
| 2019/0056371 A1 | 2/2019 | West | |
| 2019/0194034 A1 | 6/2019 | Giguere et al. | |
| 2020/0363334 A1 | 11/2020 | Das | |
| 2020/0378893 A1 | 12/2020 | Das | |
| 2021/0018442 A1 | 1/2021 | MacFarland et al. | |
| 2021/0147270 A1* | 5/2021 | Udagawa | C02F 11/185 |
| 2021/0270759 A1* | 9/2021 | Van Der Meer | G01N 1/18 |
| 2022/0261721 A1 | 8/2022 | Rajasekharan et al. | |
| 2022/0267168 A1* | 8/2022 | Kasai | C02F 1/008 |
| 2022/0268726 A1* | 8/2022 | Takehiro | G01N 21/78 |

* cited by examiner

| Growth/ Inactivation | Variables | Threshold Value |
|---|---|---|
| Growth (X) | Free ammonia | ≥ 0.5 mg/L |
|  | Nitrite | ≥ 0.5 |
|  | Nitrate | ≥ 0.05 |
|  | HPC | ≥ 100 with 100% |
|  | Temperature | >28 C |
| Inactivation(Y) | Total Chlorine | ≥ 1.5 |
|  | Mono chloramine | ≥ 1.5 |
|  | Free Chlorine | ≥ 1.5 |
|  | pH level | 7.5-8.5 |

FIG. 2

| TYPE 1 RECOMMENDATION ||
|---|---|
| Field Response | Administrative Response |
| Recheck Parameters at Site to Ensure Accuracy | Evaluate Trends and Review Historical Data for Site |
| Flush Site for 10 Minutes. Recheck Parameters. | Evaluate Effectiveness of Field Responses |
| Increase Monitoring Frequency | Communicate Findings to Department Personnel (e.g., Water Quality Manager, Water Plant Manager, etc.) |
| | Prepare for Type 2 Recommendation |

| TYPE 2 RECOMMENDATION ||
|---|---|
| Field Response | Administrative Response |
| Chlorine Sweep | Evaluate Effectiveness of Field Response |
| Valve Sweep | Communicate Findings to Personnel (e.g., Assistant Directors, Director of Water Utilities, etc.) |
| Conventional Flushing | Prepare for Type 3 Recommendation |
| Drain and Refill Nearby Tanks | |

| TYPE 3 RECOMMENDATION ||
|---|---|
| Field Response | Administrative Response |
| Localized Unidirectional Flushing Based on System Operations | Evaluate Effectiveness of Field Response |
| Drain and Refill Tanks Located Near Site(s) of Concern Based on System Operations | Communicate Findings to Department Personnel (e.g., Water Quality Manager, Water Plant Manager, etc.) |
| | Prepare for Type 4 Recommendation |

| TYPE 4 RECOMMENDATION ||
|---|---|
| Field Response | Administrative Response |
| Breakpoint Chlorination of the Entire Distribution System and Temporary Switch to Free Chlorine | Notify Regulatory Agencies of Chlorine Conversion |
| | Notify Hospital and Dialysis Clinics |
| | Work with Public Information Office and Media |
| | Follow Chlorine Conversion Protocols |

FIG. 3

| Parameter | Level 1 | Level 2 | Level 3 | Level 4 |
|---|---|---|---|---|
| Total Chlorine | < 1.75 | < 1.5 | < 1.0 | < 0.75 |
| Monochloramine | < 1.25 | < 1.0 | < 0.5 | < 0.5 |
| Free Ammonia | > 0.25 | > 0.30 | > 0.35 | > 0.40 |
| Nitrite-N | < 0.02 | < 0.03 | < 0.04 | < 0.05 |
| Nitrate -N | > 10% increase | > 20% increase | > 30% increase | > 40% increase |
| NPI | Low | Medium | High | Very High |

FIG. 4A

| Recommendation Type | Components Exceeding Action Level | Particular Action Level Number that is Exceeded |
|---|---|---|
| 1 | 2 | 1 |
| 2 | 3 | 1 |
| 2 | 2 | 2 |
| 3 | 2 | 3 |
| 3 | Site Not Improved by Option 2 Decisions ||
| 4 | 1 | 4 |
| 4 | Site Not Improved by Option 1, 2, 3 Decisions ||

FIG. 4B

PREDICTIVE MODEL FOR WATER QUALITY DETERIORATION

BACKGROUND

This application relates generally to forecasting the state of water quality in a water distribution system at a future point in time.

Ensuring water quality is critical in a number of industries such as pharmaceuticals and other manufacturing fields. Additionally, ensuring water quality is critical to the health of humans, animals, and plants which are reliant on the water for survival. Consequently, the deterioration of water quality jeopardizes both life and business. This deterioration may be a result of one or more different factors such as nitrification, corrosion, and/or disinfectant byproduct formation. Depending on the root problem, specific actions need to be taken in order to mediate further water quality deterioration and to correspondingly ensure the viability of the water distribution system.

BRIEF SUMMARY

In summary, one embodiment provides a method of forecasting water quality deterioration in a water distribution system, comprising: receiving, at an electronic device, a data set comprising measured values of a plurality of chemical components within the water distribution system; determining, based upon algorithmic analysis of the measured values, a water quality index; and providing, based on the determined water quality index, a recommendation to mitigate water quality deterioration in the water distribution system.

Another embodiment provides an electronic device for forecasting water quality deterioration in a water distribution system, comprising: a processor; and a memory storing instructions executable by the processor to: receive a data set comprising measured values of a plurality of chemical components within the water distribution system; determine, based upon algorithmic analysis of the measured values, a water quality index; and provide, based on the determined water quality index, a recommendation to mitigate water quality deterioration in the water distribution system.

A further embodiment provides a computer program product, comprising: a storage device that stores code, the code being executable by a processor and comprising: code that receives a data set comprising measured values of a plurality of chemical components within the water distribution system; code that determines, based upon algorithmic analysis of the measured values, a water quality index; and code that provides, based on the determined water quality index, a recommendation to mitigate water quality deterioration in the water distribution system.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 2 illustrates an example table containing growth and inactivation components and their requisite threshold levels according to an embodiment.

FIG. 3 illustrates an example of plurality of sample recommendation types according to an embodiment.

FIG. 4(A-B) illustrate examples of tables that identify action level thresholds for various components and the corresponding recommendation types according to an embodiment

DETAILED DESCRIPTION

Figure 1:
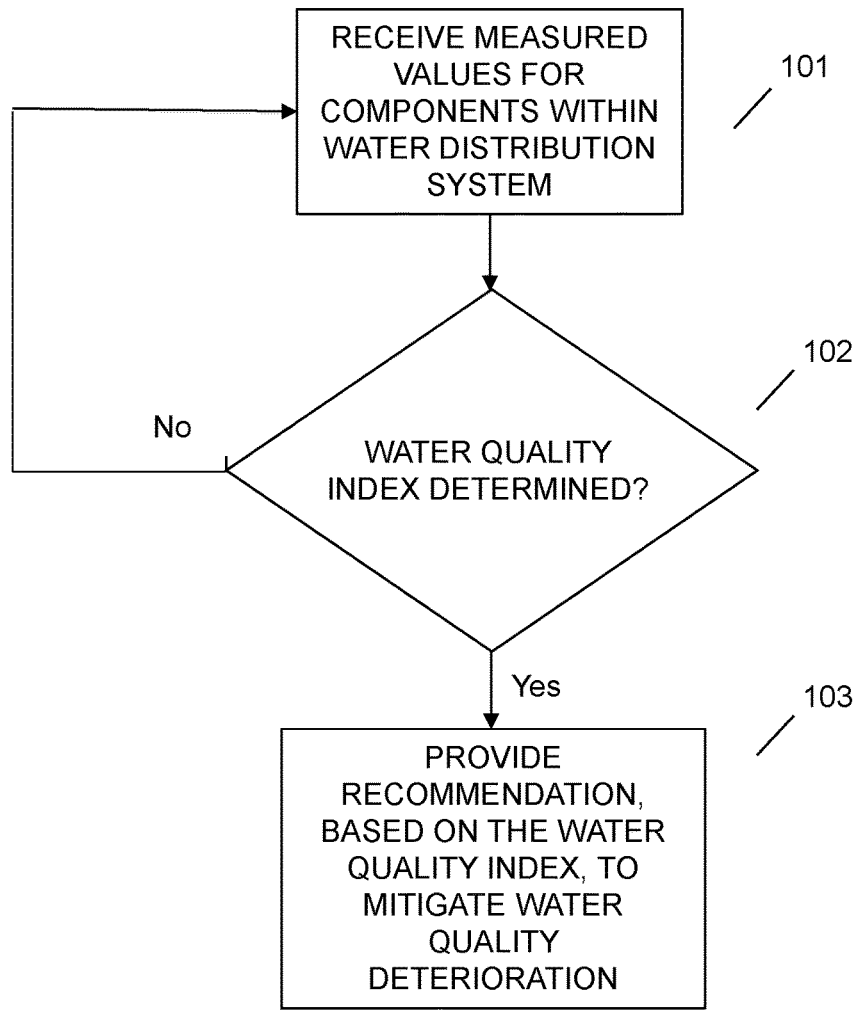
FIG. 1 illustrates a flow diagram of forecasting the water quality in a water distribution system.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

A plurality of factors may negatively affect the quality of water as the water travels from a treatment plant to an end user or entity. One factor, for example, may correspond to the corrosive effects of the water transport pipe. More particularly, certain portions of the water transport pipe may begin to shed lead, copper, or other materials over time that may mix with the water contained therein. Additionally or alternatively, small cracks in the pipe could also develop that may allow sediment and/or other materials to mix with the water and consequently degrade its quality. Another factor that may affect the water quality is the formation of disinfection byproducts from the chemicals used to treat the water. For instance, chlorine is frequently used as a disinfectant in water to prevent the growth of, or eliminate the presence of, various types of microorganisms. Although effective, excess chlorine may react with certain organics in the water to form harmful byproducts that negatively affect the water quality.

Although each of the above factors may degrade the quality of water, the majority of this application will be directed to the negative effects resulting from the process of nitrification. However, it is important to note that such a focus is not limiting, and the novel concepts described herein may be applicable to forecast the degradation of water quality resulting from other factors such as corrosion and disinfectant byproduct formation.

Nitrification is a biological process in which certain types of bacteria can proliferate by consuming one of the ingredients of the disinfectants used to treat the water. Such an issue generally occurs in treatment plants that utilize chloramine to treat the water instead of chlorine. More particularly, chloramine has an innate ability to persist longer than chlorine, which makes it ideal for distribution systems that have larger populations to serve and/or whose populations are spread out over a larger area. However, chloramine contains chlorine and ammonia which, in some conditions, may disassociate, thereby allowing the ammonia to act a nutrient for bacterial growth. As the ammonia is consumed it is converted to nitrite and nitrate, which correspondingly leads to loss of the disinfectant and subsequently enables the water quality to degrade.

Nitrification in water distribution systems is a pervasive and persistent problem that creates chronic disinfection residual challenges that are time-consuming and costly to address. If left unchecked, the health of the individuals who ultimately drink the water may be jeopardized and the water treatment facilities responsible for ensuring the water quality may be subject to regulatory violations. Conventional solutions for addressing this problem are generally reactive in nature. More particularly, remedial actions are generally not taken until the issue is bad enough that it demands action. Accordingly, forecasting the risk of nitrification may enable pro-active steps to be taken to prevent the onset of harmful process.

Accordingly, an embodiment provides a system and method for generating a water quality index value that forecasts what the water quality will be at a particular future point. Based on this index value, a tailored recommendation may be provided that outlines various steps that may be taken to mitigate the water quality deterioration for a specific contextual situation. In an embodiment, a data set containing measured values for a plurality of components associated with a water distribution system may be received at an electronic device. These components, or variables, may include chemical components (e.g., free ammonia, total chlorine, nitrite, nitrate, mono chloramine, etc.) or state conditions (e.g., temperature within the transport pipe, pH of the water, etc.). An embodiment may thereafter analyze these values using a dedicated algorithm to determine an index classification of water quality. The index classification may be a single numerical value that projects what the water quality will be at a future point in time if the current conditions persist. Based on the index classification, a tailored recommendation may be provided to a user or entity that outlines one or more suggested steps that could be taken to proactively address any forecasted deterioration to the water quality or to remediate existing issues in the water distribution system.

The illustrated example embodiments will be best understood by reference to the figures. The following description is intended only by way of example, and simply illustrates certain example embodiments.

Referring to FIG. 1, an example system and method for forecasting the quality of water at a future point in time is illustrated. At 101, a data set containing measured values for a plurality of components associated with a water distribution system may be received at a device. The components may include chemical components (i.e., free chemicals present in the water, disinfectants, disinfectant byproducts, etc.) or state conditions (e.g., the temperature of the water, the temperature within the water transport pipe at a particular location, the pH level of the water, etc.). Measurements for these components may be obtained by various conventional instruments, sensors, and/or processes either on site (i.e., within or at the water transport pipe, etc.) or at another location (e.g., a laboratory, etc.).

In an embodiment, the measurements for these components may correspond to a particular past date. The "lag" time between when the measurements were obtained and the day the analysis described herein are conducted may subsequently influence how far into the future water quality may be forecast. As a non-limiting example, measurements for components that are a day old may be able to forecast the quality of water at a point ten days into the future.

In an embodiment, each of the components may be categorized into one of two groups: a growth group and an inactivation group. With respect to the former, a presence of these components at certain levels in the water may promote the growth of certain bacteria whereas the presence of the latter at certain levels may facilitate the inactivation of bacterial growth. As a non-limiting example, and with reference to FIG. 2, a table is provided that illustrates the potential breakdown of measured components within an aqueous sample. In the growth group are byproducts of disinfectants (e.g., ammonia, nitrite, nitrate, etc.), Heterotrophic Plate Count (HPC) (i.e., a direct measure of the growth of bacteria), and measured temperature. In the inactivation group are the disinfectants themselves (e.g., total chlorine, monochloramine, and free chlorine) and a pH range of the water. It is important to note that the listing of these components is not exhaustive and measurements for a variety of other components, not explicitly described here, may also be obtained and utilized to forecast water quality. Further illustrated are threshold values for each component. These threshold values may identify a critical point that, above which, the components associated with the growth group may begin to negatively affect the water quality and that, below which, the components associated with the inactivation group may lose their effectiveness in mitigating bacterial growth.

At 102, an embodiment may determine a water quality index ("index") based upon the measured values. In an embodiment, the index may be representative of the water quality at a particular future point in time for a given context. Although such an index may be applicable to a variety of different factors (e.g., the forecasted effects of corrosion on the water quality, the forecasted effects of disinfectant byproduct formation on the water quality, etc.), the balance of this disclosure is directed to a Nitrification Potential Index ("NPI") which forecasts the projected onset of nitrification at a future point given previously obtained measurements for components in the water distribution system.

In an embodiment, the NPI may be a single, numerical figure that may be representative of the potential state of nitrification at a future point based on the measured values. Such a numerical figure may be calculated using the following algorithm:

$$P(NPI)_{(t+H)} = \frac{\beta_0 + \beta_1 X_{1(t-L)} + \beta_2 X_{2(t-L)} \ldots + \beta_n X_{n(t-L)})}{\chi_0 + \chi_1 Y_{1(t-L)} + \chi_2 Y_{2(t-L)} \ldots + \chi_n Y_{n(t-L)})}$$

This algorithm considers the measured values for the components in the water distribution system and also balances the lag time (L) from when the measurements were taken to identify a horizon time (H) for which the NPI may be applicable.

At 103, using the index classification for water quality an embodiment may provide a proactive recommendation to an individual or entity containing one or more steps that may be taken to mitigate water quality deterioration in the water distribution system. The urgency and/or complexity of the recommendation may be directly proportional to the NPI number (i.e., the greater the NPI number the more involved the suggested strategy may be to prevent further exacerbation of the nitrification process). Additionally or alternatively, the content presented within the recommendation may be influenced by other factors, as further described herein.

In an embodiment, the type of recommendation provided may be based exclusively on the NPI number. More particularly, the content in the recommendation may be dependent upon a range that the NPI number falls into (e.g., 0.5-0.75 corresponds to a Type 1 Recommendation, 0.75-1 corresponds to a Type 2 Recommendation, etc.) and wherein the critical nature of each successive recommendation is increased (e.g., a Type 4 Recommendation is more serious than a Type 2 Recommendation). The range may be originally set by a programmer of the software and may later be adjusted by a user. In an embodiment, a system of the embodiments may access this range data from an accessible source (e.g., a database stored locally on a computer device or remotely on another device or server, etc.).

In an embodiment, an NPI threshold may be designated. If the NPI is below this threshold number then bacterial growth is controlled and nitrification is not expected to occur. In such a situation, no recommendation may be provided or, alternatively, the recommendation may suggest that current processes and procedures be maintained. Conversely, if the NPI is greater than the threshold number, the onset of nitrification is expected and a recommendation that reflects the severity of the projected onset may appropriately be provided.

In an embodiment, the proactive, or occasionally reactive steps (depending on the severity of the projected situation), suggested in each recommendation may be segregated into different response categories. For example, certain steps may be designated to be performed in the field (i.e., on site at or within the water transport pipe) whereas other steps may be more administrative in nature (e.g., evaluation of field responses, communication of findings to relevant authorities, etc.). The more of these suggested steps that are performed, on both the field and administrative ends, the better the likelihood that projected issues of nitrification may be mitigated.

Referring now to FIG. 3, a non-limiting, representative example of the foregoing concepts is provided. In such a scenario, an NPI threshold may be set at 0.5, a range for a Type 1 Recommendation may be set between 0.5-0.75, a range for a Type 2 Recommendation may be set between 0.75-1, a range for a Type 3 Recommendation may be set between 1-1.25, and a range for a Type 4 Recommendation may be set between 1.25 and greater. Accordingly, if an NPI number is determined to be 0.8, the Type 2 Recommendation may be provided to an end user that suggests that, inter alia, a chlorine and valve sweep be conducted on the water transport pipe. Similarly, if the NPI number is determined to be 1.5, the Type 4 Recommendation may be provided to the end user in which a breakpoint chlorination of the entire water distribution system should be conducted. The suggested steps for both the field and administrative categories are not limited to what is illustrated in FIG. 3 but rather may be further adjusted by a programmer or end-user. The information in the tables in FIG. 3 was obtained from *Tackling One City's Nitrification Action Plan*, by Crystal Ybanez. January 2020, Vol 112, No 1, 41.

In addition to the proactive mitigation of WQ deterioration, real time mitigation recommendations may be dynamically influenced by an identification of: A) the number of components that exceed a particular action level; and/or B) the particular action level that is exceeded. Referring now to FIG. 4A, a table is provided that identifies the threshold levels for each component based upon the action level. For example, if the amount of free ammonia is determined to be 0.31, then the action level corresponding to that measurement for free ammonia is Action Level 3. Referring now to FIG. 4B, a table is provided that identifies the type of recommendation that may be provided based upon the component measurements as they relate to the action level thresholds. For instance, a Type 1 Recommendation may be provided responsive to identifying that 2 components have measured values that exceed the threshold values for Action Level 1. For example, a Type 1 Recommendation may be provided responsive to identifying that the value of total chlorine is 1.6 and the value of monochloramine is 1.15. Such a result may imply that the amount of disinfectants in the system has fallen below a first threshold level and the status of the water distribution system at least warrants some consideration. In another example scenario, a Type 4 Recommendation may be provided responsive to identifying that the measured value of just a single component has exceed an Action Level 4 threshold level.

The various embodiments described herein thus represent a technical improvement to conventional techniques for addressing issues with the water quality in a water distribution system, particularly issues resulting from the process of nitrification. Using the techniques as described herein, an embodiment may receive measured values from a plurality of components associated with the water distribution system. Thereafter, using these measured values, a water quality index may be determined. Such an index may forecast the potential for onset of issues with water quality due to one or more water quality deterioration factors (e.g., nitrification, corrosion, disinfect byproduct formation, etc.). Based upon this determined index value, an embodiment may provide a particular recommendation containing one or more steps that a user can take to mitigate the onset of the negative affects to the water quality.

Figure 5:
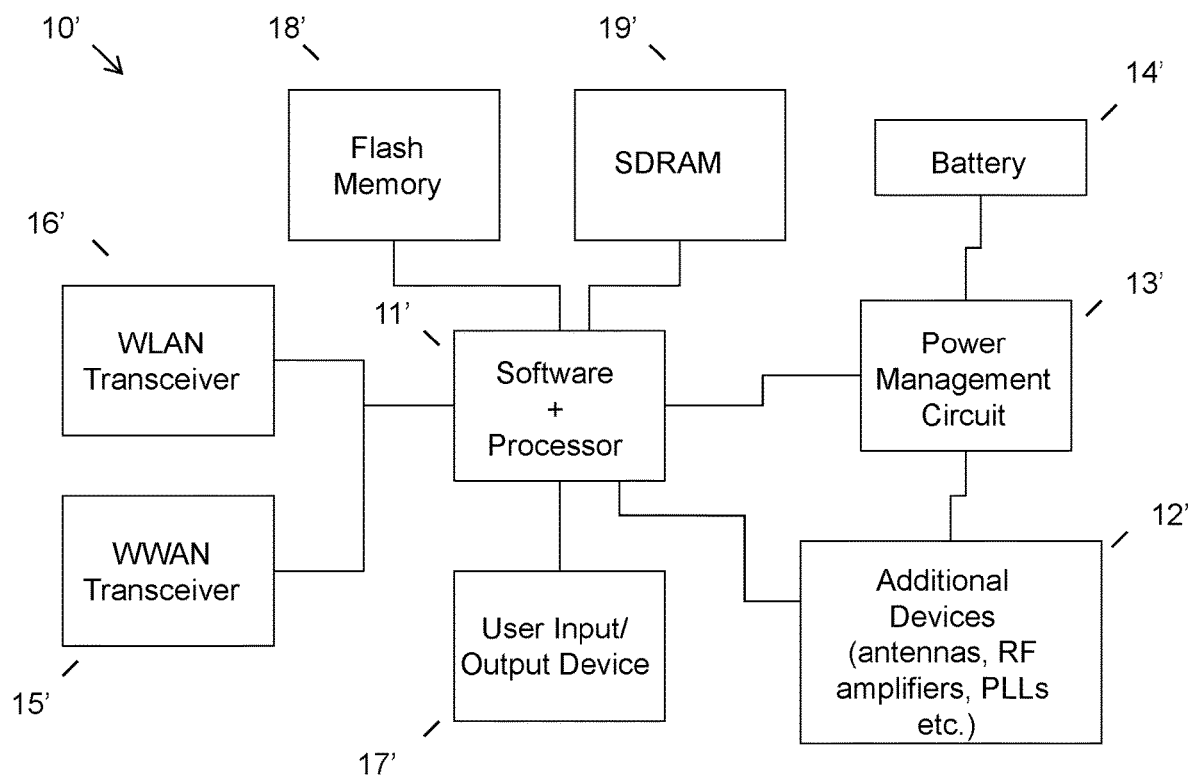
FIG. 5 illustrates an example of computer circuitry.

While various other circuits, circuitry or components may be utilized in information handling devices, regarding an instrument for measurement of copper and zinc according to any one of the various embodiments described herein, an example is illustrated in FIG. 5. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform measurement of copper and zinc of an aqueous sample.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method of forecasting water quality deterioration in a water distribution system, comprising:
   receiving, at an electronic device in real time using at least one sensor, a data set comprising measured values of a plurality of components within the water distribution system, wherein the data set comprises a growth group of at least one disinfectant byproduct and an inactivation group of at least one disinfectant, wherein the at least one sensor comprises a sensor to measure nitrite corresponding to a nitrification of the water;
   generating, based upon algorithmic analysis of the measured values, a water quality index, wherein the generating comprises:
      identifying a plurality of action levels;
      identifying a threshold value associated with each of the plurality of action levels;
      determining which of the action levels has the threshold value exceeded; and
      determining which of the plurality of components exceed the threshold value based upon the measured value;
   identifying a time duration from a time when the measured values are received and a time the water quality index reaches a threshold, wherein the threshold defines a point at which an effect of the growth group is greater than an effect of the inactivation group; and
   tailoring, based on the water quality index, the received data set from the at least one sensor, and the time duration, a recommendation to mitigate water quality deterioration in the water distribution system, the recommendation dynamically updated in real time by an identification of the number of components that exceed a threshold level, wherein the recommendation comprises a field response for the water distribution system to mitigate water quality deterioration and an administrative response to communicate the recommendation, wherein the tailoring comprises:
      providing the recommendation based on the determination at least one of: conducted chlorine and valve sweep on the water transport pipe or a breakpoint chlorination of the entire water distribution system.

2. The method of claim 1, wherein each of the plurality of components are associated with one of: bacterial growth or bacterial inactivation.

3. The method of claim 1, wherein each measured value in the data set comprising measured values of a plurality of components is selected from the group consisting of: free ammonia, nitrite, nitrate, hydroxypropyl cellulose, temperature, total chlorine, mono chloramine, free chlorine, and pH level.

4. The method of claim 1, wherein the measured values originate from a past time before a present time and wherein the index classification of water quality corresponds to a future time after the present time.

5. The method of 1, wherein the water quality index is associated with a potential for nitrification in the water distribution system.

6. The method of claim 1, wherein the water quality index corresponds to a single numerical value.

7. The method of claim 6, wherein a critical nature associated with the recommendation is directly proportional to a size of the single numerical value.

8. The method of claim 1, wherein the recommendation comprises a plurality of suggested actions and wherein a portion of the plurality of suggested actions are designated as field actions and wherein another portion of the suggested actions are designated as administrative actions.

9. An electronic device for forecasting water quality deterioration in a water distribution system, comprising: a processor; and a memory storing instructions executable by the processor to:
receive, at an electronic device in real time using at least one sensor, a data set comprising measured values of a plurality of components within the water distribution system, wherein the data set comprises a growth group of at least one disinfectant byproduct and an inactivation group of at least one disinfectant,
wherein the at least one sensor comprises a-sensor to measure a-nitrite corresponding to a nitrification of the water;
generate, based upon algorithmic analysis of the measured values, a water quality index, wherein the generating comprises:
identifying a plurality of action levels;
identifying a threshold value associated with each of the plurality of action levels;
determining which of the action levels has the threshold value exceeded; and determining which of the plurality of components exceed the threshold value based upon the measured value;
identifying a time duration from a time when the measured values are received and a time the water quality index reaches a threshold, wherein the threshold defines a point at which an effect of the growth group is greater than an effect of the inactivation group; and
tailor, based on the water quality index, the received data set from the at least one sensor, and the time duration, a recommendation to mitigate water quality deterioration in the water distribution system, the recommendation dynamically updated in real time by an identification of the number of components that exceed a threshold level, wherein the recommendation comprises a field response for the water distribution system to mitigate water Quality deterioration and an administrative response to communicate the recommendation,
wherein the tailoring comprises: providing the recommendation based on the determination at least one of: conducted chlorine and valve sweep on the water transport pipe or a breakpoint chlorination of the entire water distribution system.

10. The electronic device of claim 9, wherein each of the plurality of components are associated with one of: bacterial growth or bacterial inactivation.

11. The electronic device of claim 9, wherein each measured value in the data set comprising measured values of a plurality of components is selected from the group consisting of: free ammonia, nitrite, nitrate, hydroxypropyl cellulose, temperature, total chlorine, mono chloramine, free chlorine, and pH level.

12. The electronic device of claim 9, wherein the measured values originate from a past time before a present time and wherein the index classification of water quality corresponds to a future time after the present time.

13. The electronic device of claim 9, wherein the water quality index to a single numerical value.

14. The electronic device of claim 9, wherein a priority level associated with the recommendation is directly proportional to a size of the single numerical value.

15. The electronic device of claim 9, wherein the recommendation comprises a plurality of suggested actions and wherein a portion of the plurality of suggested actions are designated as field actions and wherein another portion of the suggested actions are designated as administrative actions.

16. A computer program product, comprising: a non-transitory storage device that stores code, the code being executable by a processor and comprising: code that receives, at an electronic device in real time using at least one sensor, a data set comprising measured values of a plurality of components within the water distribution system, wherein the data set comprises a growth group of at least one disinfectant byproduct and an inactivation group of at least one disinfectant, wherein the at least one sensor comprises a sensor to measure nitrite corresponding to a nitrification of the water;
code that generates, based upon algorithmic analysis of the measured values, a water quality index, wherein the generating comprises:
identifying a plurality of action levels;
identifying a threshold value associated with each of the plurality of action levels;
determining which of the action levels has the threshold value exceeded; and
determining which of the plurality of components exceed the threshold value based upon the measured value;
identifying a time duration from a time when the measured values are received and a time the water quality index reaches a threshold, wherein the threshold defines a point at which an effect of the growth group is greater than an effect of the inactivation group; and
code that tailors, based on the water quality index, the received data set from the at least one sensor, and the time duration, a recommendation to mitigate water quality deterioration in the water distribution system, the recommendation dynamically updated in real time by an identification of the number of components that exceed a threshold level,
wherein the recommendation comprises a field response for the water distribution system to mitigate water quality deterioration and an administrative response to communicate the recommendation, wherein the tailoring comprises: providing the recommendation based on the determination at least one of: conducted chlorine and valve sweep on the water transport pipe or a breakpoint chlorination of the entire water distribution system.

* * * * *